US005773672A

United States Patent [19]
Harrod et al.

[11] Patent Number: 5,773,672
[45] Date of Patent: Jun. 30, 1998

[54] PRODUCTION OF 1-BROMOPROPANE

[75] Inventors: William B. Harrod, Minden; Alireza M. Dadgar; Phillip R. Beaver, both of Baton Rouge, all of La.

[73] Assignee: Albemarle Corporation, Richmond, Va.

[21] Appl. No.: 867,144

[22] Filed: Jun. 20, 1997

[51] Int. Cl.$^6$ .................................................. C07C 17/00
[52] U.S. Cl. ............................................................ 570/249
[58] Field of Search ............................................. 570/249

[56] References Cited

U.S. PATENT DOCUMENTS

| | | | |
|---|---|---|---|
| 2,058,465 | 10/1936 | Kharasch | 260/162 |
| 2,058,466 | 10/1936 | Kharasch | 260/162 |
| 2,307,552 | 1/1943 | Vaughan et al. | 204/163 |
| 2,790,013 | 4/1957 | Barnes | 260/663 |
| 3,679,759 | 7/1972 | Schmerling | 260/663 |

FOREIGN PATENT DOCUMENTS

| | | | |
|---|---|---|---|
| 668159 | 3/1952 | United Kingdom . | |
| 927114 | 5/1963 | United Kingdom | 570/249 |

OTHER PUBLICATIONS

Brouwer, et al., "On the Addition of Gaseous Hydrogen Chloride and Hydrogen Bromide to Propane under the Influence of Catalysts", Recueil Des Travaux Chimiques Des Pays–Bas, vol. 53, 1934, pp. 1001–1010.

Hertog et al., "Addition Reactions of Alkenes in Silent Electrical Discharges[1])", Proceedings of the Koninklijke Nederlandse Akademie Van Wetenschappen, vol. 54, 1951, pp. 379–386.

Kharasch, et al., "The Peroxide Effect in the Addition of Reagents to Unsaturated Compounds", J. Amer. Chem. Soc., vol. 56, Jun. 1934, p. 1425.

Kharasch, et al., "The Peroxide Effect in the Addition of Reagents to Unsaturated Compounds. III. The Addition of Hydrogen Bromide to Propylene", J. Amer. Chem. Soc., 1933, vol. 55, pp. 2531–2533.

Vaughan, et al., "The Photo–Addition of Hydrogen Bromide to Olefinic Bonds[1]", J. of Org Chem, 1942, vol. 71, pp. 477–490.

*Primary Examiner*—Alan Siegel
*Attorney, Agent, or Firm*—E. E. Spielman, Jr.

[57] ABSTRACT

1-Bromopropane is produced from hydrogen bromide, propene and a catalytically effective amount of an ozonide catalyst and/or one or more active catalytic species formed in situ therefrom. In addition to being highly efficient and highly suitable for use on an industrial scale, the process has the additional advantages of being environmentally friendly, operationally safe, and conservationally beneficial.

24 Claims, 3 Drawing Sheets

5,773,672

1

PRODUCTION OF 1-BROMOPROPANE

TECHNICAL FIELD

This invention relates to an improved process for producing 1-bromopropane (also known as n-propyl bromide).

BACKGROUND

1-Bromopropane is an important industrial solvent for use in several different applications. Heretofore it has been manufactured commercially by the hydrobromination of 1-propanol. A need has arisen for a more cost-effective 1-bromopropane synthesis process also suitable for use on an industrial scale.

Other known methods for synthesis of 1-bromopropane exist. Kharasch et al., *J. Am. Chem. Soc.* 1933, 55, 2532–3, describe addition of hydrogen bromide to propene in the presence of peroxides such as benzoyl peroxide or ascaridole to form n-propyl bromide in high yields. See also Kharasch U.S. Pat. No. 2,058,466. Vaughan et al., *J. Org. Chem.* 1942, 7, 477–90, describe synthesis, inter alia, of n-propyl bromide by photohydrobromination of propene in liquid phase at −78° C. in quartz and in vapor phase at 25° C. in Pyrex glassware. See also Vaughan et al. U.S. Pat. No. 2,307,552. Formation of n-propyl bromide from vapor phase reaction of hydrogen bromide and propene in the presence of activated carbon catalyst is described in U.S. Pat. No. 2,790,013 to Barnes. U.S. Pat. No. 3,679,759 to Schmerling reports preparation of n-propyl bromide from concentrated hydrobromic acid and propylene at 225° C. and 30–74 atmospheres pressure. British 668,159 reports formation of 1-bromopropane by passing a mixture of 2 parts by volume of propene and 3 parts of hydrogen bromide gas at the rate of 300 cc per minute into a Siemans-type glass ozonizer kept at 20° C. and in which the distance between the inner and outer tubes was 2.5 millimeters and the volume of the discharge space was about 150 cc. The mixture in the ozonizer was exposed to silent electric discharges with a potential difference of 20,000 volts and a frequency of 50 cycles per second.

Heretofore, long chain liquid olefins having in the range of 8 to 18 carbon atoms in the molecule have been hydrobrominated with excess HBr to form long chain alkyl bromides. In the operation a stream of the olefins is treated with ozone and the resultant ozonide is promptly passed into the reactor to catalyze the hydrobromination reaction.

SUMMARY OF THE INVENTION

This invention provides a process for producing 1-bromopropane (n-propyl bromide) which, in addition to being highly efficient and highly suitable for use on an industrial scale, has the additional advantages of being environmentally friendly, operationally safe, and conservationally beneficial.

In accordance with this invention, 1-bromopropane is produced from hydrogen bromide, propene and a catalytically effective amount of an ozonide catalyst and/or one or more active catalytic species formed in situ therefrom. Thus in one embodiment a process is provided wherein a mixture is formed from hydrogen bromide, propene and a catalytically effective amount of a preformed ozonide catalyst and the mixture is subjected to and/or maintained under reaction conditions effective to produce 1-bromopropane such that 1-bromopropane is the principal product formed in the reaction. Excellent results are achieved by proportioning the hydrogen bromide and propene such that there is a stoichiometric excess of propene relative to the hydrogen bromide.

In another embodiment a process is provided wherein (a) a reaction mixture is formed from hydrogen bromide, propene, recycled reaction mass, and a catalytically effective amount of a preformed ozonide catalyst and/or one or more active catalytic species formed in situ therefrom; (b) the mixture is subjected to and/or maintained under reaction conditions effective to produce 1-bromopropane such that a reaction mass containing 1-bromopropane is produced; (c) a minor portion of the reaction mass is periodically or continuously separated therefrom; and (d) a major portion of the reaction mass is periodically or continuously recycled to the reaction mixture. Preferably, the reaction mass recycled to the reaction mixture contains residual ozonide catalyst and/or one or more active catalytic species formed in situ therefrom. In this embodiment, fresh preformed ozonide is one of the ingredients initially used in forming the mixture in (a). Thereafter, fresh hydrogen bromide, fresh propene and fresh preformed ozonide are periodically or continuously introduced to the reaction mixture, the fresh preformed ozonide being introduced in catalytically effective amounts sufficient to sustain the reaction. Here again, an excess of propene relative to HBr gives excellent results.

In all of the above embodiments the fresh preformed ozonide catalyst introduced to the reaction mixture is a material formed from interaction between ozone and one or more olefins. As used in this description including the appended claims, the term "fresh" as applied to the ozonide catalyst is used in the sense that the ozonide catalyst being referred to is unused catalyst as distinguished from recycled (used) catalyst and/or recycled catalyst species and/or residues. The fresh catalyst can be taken from storage and thus need not be freshly prepared. For example, ozonide catalyst made from $C_{14}$ alpha-olefin has been found to have half lives of 179 hours at 71°–77° F. (ca. 22° to 25° C.) and 248 hours at 41° F. (5° C.).

Likewise, the term "fresh" as applied to hydrogen bromide and propene is used in connection with embodiments involving recycle of reaction mass. In such cases the term "fresh" is used to distinguish (a) the hydrogen bromide and propene being introduced for the first time to the reactor, from (b) the hydrogen bromide and propene that are being returned to the reactor as recycled materials.

The reaction between hydrogen bromide and propene can be performed with the hydrogen bromide (HBr) and propene reactants in the liquid phase and/or in the vapor phase. Conversions as high as about 97% or more based on HBr can be achieved by use of suitable reaction conditions.

Despite the fact that one of the reactants in the process, propene, is a highly flammable, gaseous material, and that the fresh catalyst is chemically a highly active substance, the process of this invention is advantageous because it can be efficiently and safely operated on a large scale. The process is also highly advantageous in that it utilizes two reactants which in large measure are produced as co-products of other industrial processes, and thus the process conserves resources which might otherwise be wasted, while at the same time converting them with high (but not necessarily complete) specificity to a highly useful industrial product, 1-bromopropane. Typically at least about 96% of the product formed is 1-bromopropane with the balance, if any, being substantially entirely 2-bromopropane, plus perhaps trace amounts of one or more impurities. Because the process is so highly efficient, the proportion of co-products requiring disposal are minimal, and thus the process is an environmentally wholesome operation.

It is desirable in most cases to conduct the hydrobromination process of this invention at one or more temperatures in the range of about 10° C. to about 60° C. and at one or more pressures in the range of about 0 to about 60 psig, and preferably in the range of about 10 to about 30 psig. However, other conditions are suitable for use in the process, as will be apparent from the description hereinafter.

Other embodiments and features of the invention will be still further apparent from the ensuing description and appended claims.

FURTHER DETAILED DESCRIPTION

Ozonide Catalyst

Figure 1:
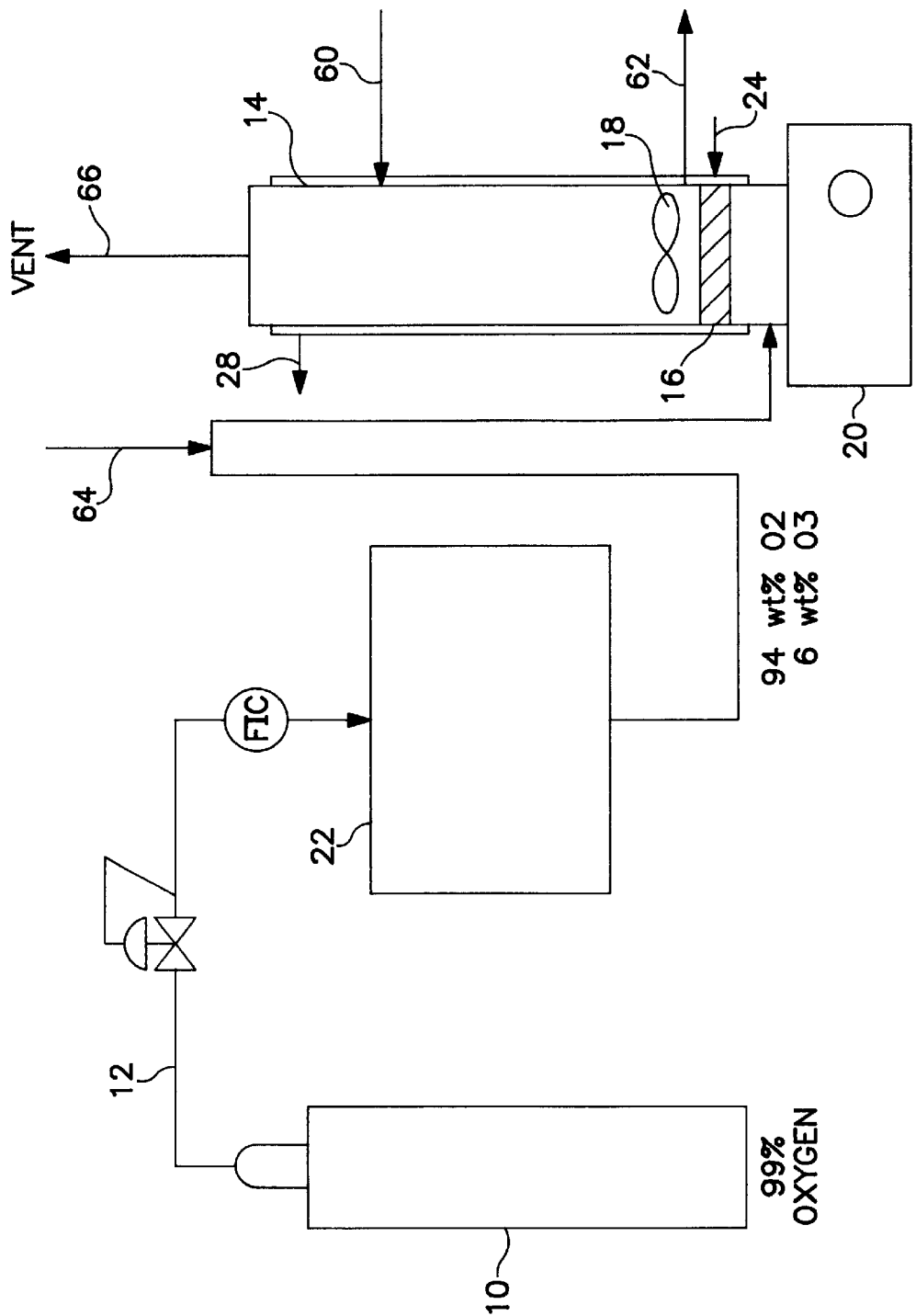
FIG. 1 is a schematic flow diagram of apparatus for producing preformed ozonide catalyst for use in the process of this invention.

In the practice of this invention the fresh catalyst ingredient or component as fed into the reaction mixture is an ozonide preformed from one or more suitable olefins, e.g., one or more olefins having in the range of about 5 to about 30, and preferably in the range of about 8 to about 18, carbon atoms in the molecule. Of the foregoing olefins, those which exist in the liquid state at 20° C. and atmospheric pressure are preferred over olefins that under the same conditions are in the solid or waxy state, as the liquid olefins are more easily handled and used in forming ozonides. Thus mixtures of olefins which have an average number of carbon atoms in the range of about 5 to about 30 can be used even if individual species of the mixture fall outside this range, especially where the mixture is itself in the liquid state at 20° C. and atmospheric pressure. Pure ozonides of ethene and/or propene are not recommended because they can pose explosion hazards. A most preferred ozonide is formed from one or more $C_{14}$ olefins, which optionally may contain small amounts (e.g., up to about 5–10 wt %) of $C_{12}$, $C_{13}$, $C_{15}$, and/or $C_{16}$ olefin(s). Despite their enhanced safety characteristics, reasonable care should be exercised when handling or using $C_5$ or higher ozonides especially if they are in a concentrated state. Ethyl ozonide and propyl ozonide are shock sensitive materials, and it is possible that in the pure state higher members of the series may also exhibit shock sensitivity. Thus higher members of the series should also be treated with due care. To enhance safety, the ozonide catalysts in the form initially fed to the reaction mixture pursuant to this invention are typically solutions containing the catalyst in diluted form in a suitable solvent, preferably 1-bromopropane. The catalyst solution typically will also contain a small amount of unreacted liquid olefin(s) from which the ozonide has been prepared. Other suitable solvents include inert liquid hydrocarbons of appropriate boiling temperatures such as liquid paraffins or cycloparaffins.

As noted above, in conducting the process of this invention, fresh ozonide catalyst is introduced into the hydrobromination reactor, and when the process is conducted with recycle flows, some recycled ozonide catalyst and/or residues/species formed in situ therefrom are returned to the hydrobromination reactor.

The catalytically effective amount of olefin ozonide catalyst and/or catalytic species formed in situ therefrom maintained in the reaction mass is an amount that is at least sufficient to sustain the hydrobromination reaction. Typically the amount falls in the range of about 0.005 to about 1 mole % of catalyst (calculated as olefin ozonide) based on the total moles of reacted and unreacted propene and HBr in the reaction mass. Preferably the amount of catalyst (calculated as olefin ozonide) is in the range of about 0.02 to about 0.4 mole % based on the total moles of reacted and unreacted propene and HBr in the reaction mass. It is particularly preferred to maintain in the reaction mass an amount of the ozonide catalyst and/or catalytic species formed in situ therefrom falling in the range of about 0.04 to about 0.16 mole % of catalyst (calculated as olefin ozonide) based on the total moles of reacted and unreacted propene and HBr in the reaction mass. In preferred embodiments where a recycle stream of reaction mixture is fed back to the reactor, e.g., as a downward countercurrent flow relative to the upward flow of reactants in the vapor phase, the amount of catalyst and/or catalytic species formed in situ therefrom maintained in the reaction mass should take into consideration both the amount of fresh catalyst and fresh reactants (fresh propene and fresh HBr) being fed to the reactor, and the amount of catalyst and/or active catalytic species, and bromopropanes (and unreacted propene and HBr, if any) being returned to the reactor via the recycle stream. The optimal amounts of fresh catalyst fed to the reactor after reaction initiation where recycle of reaction mixture is being used will thus vary to some extent depending, for example, on such factors as the amount of recycled reaction mixture being returned to the reactor; the amount of fresh catalyst previously fed to the reaction mixture; and the presence or absence of impurities that can interfere with, inhibit or even negate the catalytic activity of the ozonide catalyst or catalytic species thereof such as water, iron, alcohols, etc. Indeed it is theoretically possible under ideal conditions to operate with recycle of reaction mixture and without feed of fresh ozonide catalyst once the reaction has been properly initiated, although achieving such ideal conditions in a large-scale industrial facility may not be possible. Thus, in any given situation it is desirable to perform a few preliminary experiments to optimize the rate and amount of fresh catalyst feed under the particular set of operating conditions selected for use.

Fresh ozonide catalyst can be fed to the reactor continuously or periodically, as long as there is sufficient catalyst or active catalyst species or residues present in the reaction mixture to sustain the reaction at the desired rate.

It will be understood and appreciated that the ozonide catalyst may possibly undergo one or more changes in chemical composition during the hydrobromination reaction, and that the actual catalytic species may differ in composition from that of the initial ozonide. Thus, reference to the ozonide catalyst herein is to the ingredient or component as it exists when initially formed and before it comes in contact with any other substance. If the ozonide does undergo one or more changes when performing its function as catalyst in the desired anti-Markownikoff hydrobromination reaction, such change or changes is/are within the scope of this invention, as such change(s), if any, is/are the natural consequence of performing the process of this invention in accordance with the disclosure hereof. It is also to be understood and appreciated that the term "catalyst" is used throughout the disclosure and claims hereof to denote only that the material makes it possible for the desired anti-Markownikoff hydrobromination reaction to take place. The term does not mean, imply or suggest any mechanism or specific way by which the material performs the function of making such desired hydrobromination reaction take place.

Without in any way limiting the generality of the foregoing, the catalyst may function as a reaction initiator, and/or it may operate in one or more other ways. But however it operates, it enables the reaction to proceed in the desired manner, and this is the underlying reason for its use.

FIG. 1 depicts the flows in a reaction system for use in preparing preformed ozonide catalyst. Gaseous oxygen (e.g., of 99% purity) is fed from storage vessel 10 via line 12 at a suitable flow rate (e.g., 6 SCFH) to a continuous ozone generator 22 to produce a stream containing approximately 6 wt % ozone and approximately 94 wt % oxygen. Liquid olefin (most preferably $C_{14}$ alpha olefin) is charged via line 60 into jacketed column reactor 14 equipped with bottom feed gas dispersers. Product ozonide is removed from the reactor via line 62. To ensure adequate temperature control, cooling fluid is continuously passed into the jacket of reactor 14 at 24 and is continuously withdrawn from the jacket at 26. On a laboratory scale, reactor 14 can be a 2-inch (inner diameter) 8-inch long jacketed glass column equipped with a glass frit 16 to serve as a bottom feed gas disperser. Additional mixing is provided by means of a stirrer 18 which on a laboratory scale can be a magnetic stirrer actuated by stirring motor 20. The ozone stream enters at the bottom of column 14 which typically is operated at room temperature (e.g., about 22° to about 25° C.) and atmospheric pressure, wherein a mixture of the olefin ozonide and unreacted olefin is formed. To avoid any potential for explosion, the oxygen and the unreacted ozone gases entering the ozonization column should be diluted to below 8% $O_2$ with nitrogen or other inert gas, e.g., via line 64, to keep the oxygen content of the gas mixture below explosion limits. Gases leaving the reactor via line 66 should be treated to ensure destruction of any residual ozone before release to the environment.

Propene Hydrobromination Reaction

As noted above, pursuant to this invention 1-bromopropane is produced by subjecting hydrogen bromide, propene and a catalytically effective amount of the preformed ozonide catalyst to reaction conditions effective to form 1-bromopropane. The propene hydrobromination process can be conducted in the liquid phase or in a gaseous phase, and in some reaction systems part of the hydrobromination can be occurring in the vapor phase and part can be occurring in a liquid phase.

The preformed ozonide catalyst can be introduced into the reaction system in various ways. For example, the preformed ozonide can be introduced directly into a vapor phase mixture of hydrogen bromide and propene, or it can be introduced directly into a liquid phase such as a volume of 1-bromopropane containing hydrogen bromide and propene or into which hydrogen bromide and propene are also being fed. In one of the preferred embodiments of this invention the preformed ozonide catalyst is introduced in the form of a spray or mist into a vapor phase mixture of hydrogen bromide and propene.

The hydrobromination of propene can be conducted as a batch, semi-continuous or continuous process. The liquid phase reaction is best suited for continuous operation wherein HBr and propene gases are fed to a continuous reaction taking place in a body of liquid such as 1-bromopropane. In this case the constant mixing of the liquid phase provides the necessary contacting between the feed gases and the ozonide catalyst and/or active catalytic species derived therefrom. In a vapor phase reaction, the reaction is carried out in a reactive distillation apparatus such as a packed or tray column such that there is countercurrent flow contacting of the catalyst and the HBr and propene reactants being fed to the column. While various arrangements of such feeds are possible, it is desirable to feed the HBr and propene, either separately or in admixture with each other, into the lower region of the column below or into the lower part of the packing or trays, and to introduce the ozonide catalyst at an upper region of the column, preferably as a spray or mist, above or into the upper part of the packing or trays.

Although the reaction can be performed with an excess of either HBr or propene, it is distinctly preferable to operate with an excess of the propene relative to the HBr. Thus in preferred embodiments, the molar ratio of propene to hydrogen bromide used in forming the reaction mixture is above 1.0, e.g., in the range of above 1.00 to about 1.50 moles of propene per mole of HBr, and preferably in the range of about 1.005 to about 1.060 moles of propene per mole of HBr.

When conducting the process with a backflow reactor having a superposed packed or tray column, the hydrobromination of propene will usually involve one or more reaction temperatures in the range of about 10° to about 150° C. (e.g., in the range of 15° to about 70° C.) while at one or more pressures in the range of about 0 to about 100 psig (e.g., in the range of about 0 to about 50 psig) effective to produce 1-bromopropane and sufficient to maintain a liquid phase of solvent (preferably 1-bromopropane) in the sump of the reactor. Preferred conditions for a system using a backflow reactor involve temperatures in the range of about 60° to about 100° C. and pressures in the range of about 8 to about 30 psig sufficient to maintain a liquid phase in the sump of the reactor. When conducting the process in the vapor phase such as in a reactive distillation apparatus such as a packed or tray column, the reaction temperatures will typically be in the range of about 15° to about 90° C. with pressures in the range of about 4 psia to about 50 psig. Preferred reaction temperatures for such vapor phase operation are in the range of about 70° to about 95° C., with pressures in the range of about 0 to about 3 psig.

Figure 2:
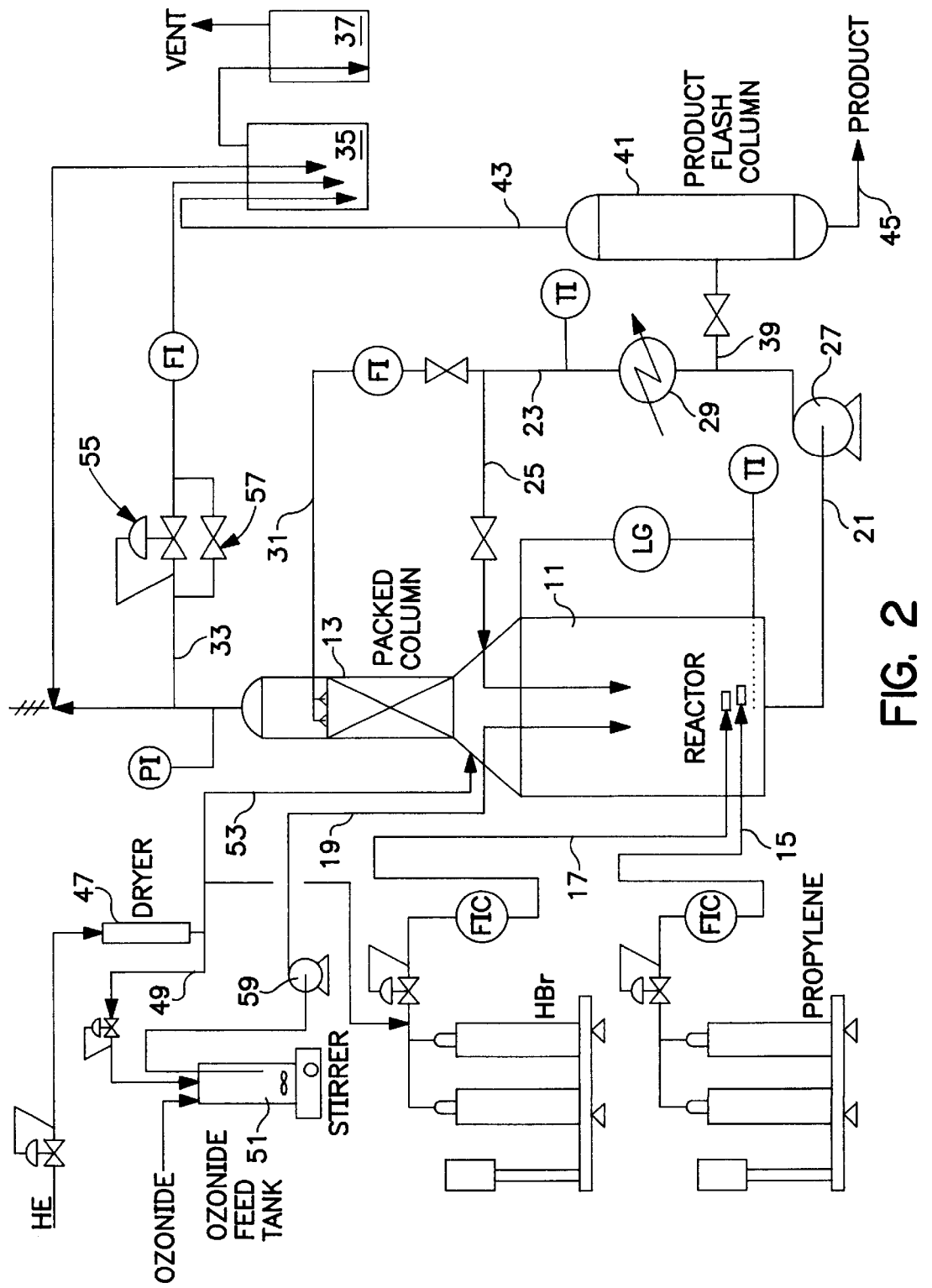
FIG. 2 is a schematic flow diagram of a process of this invention conducted in a backflow reactor having a packed column.

A preferred propene hydrobromination reaction system involving use of a backflow reactor having a packed column is illustrated in FIG. 2. In the system depicted, reactor 11 is equipped with superposed packed column 13. Propene and hydrogen bromide are fed via lines 15 and 17, respectively, into the lower region of reactor 11 and directly into a reaction mixture composed predominately of liquid 1-bromopropane into which preformed ozonide catalyst is fed via line 19. Reactor 11 is equipped with a pump-around loop composed of lines 21, 23, 25 and 31, pump 27 and heat exchanger 29. Line 31 transmits a portion of the flow from line 23 into an upper region of packed column 13. It is discharged in the upper region of column 13 as a spray to form a downward flow in countercurrent relationship to the upward flow of that portion of the propene and hydrogen bromide that have not reacted in the body of the liquid 1-bromopropane in reactor 11. Any gases escaping from the top of column 13 are transmitted via line 33 into water scrubber 35, and thence into scrubber 37 containing a suitable basic scrubbing solution, such as a 25% aqueous sodium hydroxide solution. A portion of the reaction mass in line 21 composed predominately of 1-bromopropane is transferred via line 39 to product flash column 41 where volatiles are stripped off and transferred via line 43 to caustic scrubber 35, and product 1-bromopropane (typically along with a very small amount of 2-bromopropane) is recovered via product transfer line 45. Inert gas such as helium or argon dried in column 47 is introduced via line 49 into the ozonide catalyst solution in ozonide feed tank 51 during startup and shutdown, and via line 53 into the vapor space of reactor 11 above the body of liquid therein to keep water out of the system.

The packing components in column 13 are preferably constructed of Kynar polymer lined pipe spool pieces. The inlet and outlet ports (not specifically depicted) are spacers fabricated from solid discs of Kynar polymer that are fitted between the spool pieces. All wetted parts of the reactor components, including the above-referred-to pump-around loop and product transfer line, packed column, and ozonization reactor are preferably made of an acid-resistant material such as Kynar polymer or Teflon polymer. Teflon jacketed thermocouples "TI" are used to measure reaction temperature inside reactor and also in the flow just after it leaves heat exchanger 29.

It is also important to minimize and where appropriate, monitor, the content of metals such as iron in the reaction mixture so that the content is kept below about 10 ppm (wt/wt), as iron (and probably some other heavy metals) will decompose the catalyst. Thus in addition to providing resistance against acid corrosion, interior surfaces within the reaction equipment that come in contact with the catalyst or the reaction mixture are preferably lined with and, where applicable, fabricated from materials such as Kynar polymer, Teflon polymer, glass, or the like, so as to minimize the amount of metal contamination in the materials being handled and/or processed.

Before transmission via line 31 for use in forming the downward countercurrent flow in column 13, the flow in line 31 is preferably cooled by heat exchanger 29 to a temperature in the range of about −10° C. to about 65° C.

As noted above, it is highly desirable to divide the reaction mass from line 21 into the flow in line 31 (the "recycle flow"), and the flow in line 39 to product flash column 41 (the "product flow"). Preferably, a major portion of the reaction mass is the recycle flow that results in the downward liquid flow in the packed or trayed column that captures much, if not most, of the upward flow of the gaseous propene and HBr that has not reacted in the liquid phase in the reactor. Accordingly, only a minor portion of the circulating reaction mass in line 21 is transmitted to the product flash column 41 as the product flow. The optimal ratio between the recycle flow and the product flow depends upon several factors including sump operating pressure, and temperature differential between the sump temperature and the temperature to which the flow of reaction mixture has been cooled by means of heat exchanger 29. For example, when operating with sump pressure in the range of about 8 to about 30 psig, sump temperature of about 150° F. (ca. 66° C.) and a flow of reaction mass cooled by heat exchanger 29 to about 110° F. (ca. 43° C.), preferred ratios are in the range of about 41 to about 43 parts of flow returned to the reactor per each part of flow sent to the product column. Similarly, when operating with sump pressures in the range of about 8 to about 30 psig, preferred ratios are in the range of about 33 to about 35 parts of flow returned to the reactor per each part of flow sent to the product column under the following conditions: (a) sump temperature of about 140° F. (60° C.) and a flow of reaction mixture cooled by heat exchanger 29 to about 90° F. (ca. 32° C.), (b) sump temperature of about 150° F. (66° C.) and a flow of reaction mixture cooled by heat exchanger 29 to about 100° F. (ca. 38° C.), and (c) sump temperature of about 160° F. (71° C.) and a flow of reaction mixture cooled by heat exchanger 29 to about 110° F. (ca. 43° C.).

Particularly preferred ranges of operating conditions for a backflow reactor having a packed or trayed column are as follows:

| Operating Condition | Preferred Operating Range |
| --- | --- |
| Sump operating pressure | ca. 8 to ca. 30 psig |
| Sump operating temperature | ca. 54 to ca. 72° C. |
| Temperature of recycle flow to reactor | ca. 32 to ca. 44° C. |
| Ratio, recycle flow:product flow | ca. 30 to ca. 45 parts recycle flow per part of product flow |

In a particular laboratory scale installation of the type of FIG. 2, the reactor section was designed for 2800 mL of liquid volume at the 15-inch level. A 1-inch by 12-inch packed column was installed directly above the reactor to absorb unreacted HBr and propylene gases in the liquid phase supplied by the pump around loop. The column was packed with Halar Goodloe packing made by Glitsch. A glass liquid distributor designed to minimize channeling in the packed column was fitted at the top of the packed section. Additional space above the packed column was provided for vapor-liquid disengagement. The system was equipped with a safety relief device set at 50 psig. The reactor pressure was maintained through the back pressure regulator valve 55 or through the manual bypass 57 to caustic scrubber 35, and then to water scrubber 37 prior to venting. In FIG. 2, "PI" is a pressure gauge.

Additionally, the laboratory scale reactor was equipped with a liquid level gauge, "LG", consisting of a ⅜-inch OD clear Teflon tubing attached at one end to the bottom of the reactor and at the other end to the section at the top of the reactor just below the column. Heat removal and addition were made possible through above-referred-to pump-around loop in which pump 27 was a 2.5-gallon per minute Widen positive displacement, diaphragm pump made of Teflon polymer. Heat exchanger 29 consisted of a 35-foot long, ⅜-inch OD, Teflon tubing coiled inside of a refrigerated bath. A small portion of the pump discharge, representing product, was directed to product flash column 41. The major portion of the pump discharge was sent to the exchanger 29, after which, it was split to supply fluid to the top of column 13 and also directly to reactor 11 to provide column control. The liquid flow to the column was maintained at about 80% of the flooding according to flood data available from Glitsch. Product was removed at the pump discharge by adjusting a fine needle valve while keeping the level constant in the reactor. Teflon check valves and liquid seal legs were installed in all feed transfer lines to avoid back flow of fluids into the supply lines.

The HBr and propylene gases entered the laboratory scale reactor at the bottom through separate fine glass gas dispersers. Each gas supply line was manifolded separately to allow for a quick changeover and uninterrupted feed during the continuous reactor operation. The HBr and propylene gas flow rates were maintained by separate Tylan General control valves operated by a multipoint Tylan General mass flow controller, "FIC".

In the operation of the laboratory scale system just described, the concentrated ozonide catalyst was diluted with 1-bromopropane and was charged into a 600 mL Fisher Porter tube suited for low pressure operations. The ozonide feed tank was pressurized with helium to 10 psig and was transferred to the reactor by means of a low flow peristaltic pump 59. To ensure homogeneity of the catalyst, the contents of the ozonide feed tank 51 were agitated by a magnetic stirrer. Bottled helium was used to pressurize and purge the reactor to avoid any water contamination, as water renders the catalyst ineffective and forms unwanted waste hydrocarbons. For added protection against water, drying filters were installed in the helium supply line.

Prior to each run, the system was pressure checked with helium to 40 psig. The safety relief valve was set at 50 psig. Reactor 11 was, initially, charged with commercially-available 1-bromopropane (99.5 wt % purity). The refrigerated bath was set initially to 10° C. (50° F.) and was gradually raised to higher temperatures to maintain the desired reaction temperature. Next, the circulation pump 27 was started to cool the reactor contents and supply fluid to column 13. The liquid flow to the column was maintained at 80% of the flood rate by monitoring the position of the float ball inside the in-line Teflon polymer flow meter, "F1". The back pressure regulator was set at 34 psig. When the bath temperature and the reactor temperature were within 5° F. (ca. 2.8° C.) from each other, the propylene gas was introduced to the reactor. The propylene gas flow was set at 5 wt % excess of the HBr flow. Simultaneously, the ozonide solution (diluted $C_{14}$ ozonide in 1-bromopropane) was pumped at a rate to deliver the desired catalyst concentration by means of low flow peristaltic pump 59. A 10 psig helium pad was maintained in the ozonide feed tank.

As propylene feed exceeded the solubility limit in 1-bromopropane, the reactor pressure began to rise, at which point, the HBr gas was introduced at half the set point, and gradually was increased, to full scale over a 5-minute period. While monitoring the reactor pressure during the start up, excess pressure was vented through the manual bypass intermittently. As propylene and HBr feed rates stabilized, the cooler set point was gradually varied to maintain the reactor temperature at the desired condition.

Throughout the run, the propylene and HBr flow rates and weight loss, reactor temperature, cooler return temperature, bath temperature, reactor pressure, ozonide feed tank level, and liquid level in the reactor were recorded. The propylene flow rate was frequently adjusted after each reading to ensure 5 wt % excess propylene feed. As the desired reaction temperature was reached (which normally was about 65° C. (148°–150° F.), the product level in the reactor was kept constant by adjusting the manual product valve. The bottled propylene and HBr gases contained 1% propane and about 0.5% HCl, respectively. These impurities do not participate in the reaction and thus act as inerts throughout the reaction. Therefore, the system had to be vented. The system was operated at steady state for 1 hour before retaining any product for yield measurements. The reactor content was sampled every hour during each run that normally lasted three residence times (except for the first run, only one resident time). GC analysis was used to determine the selectivity to normal propyl bromide according to the expression:

% Selectivity=[1 BP/(1 BP+2 BP)]×100 where 1 BP is the weight of 1-bromopropane formed and 2 BP is the weight of 2-bromopropane formed.

Initially, a 10 mole % excess HBr relative to propene was fed. However, during the course of the experimental program it was found that use of excess propene gave superior results, both from the standpoint of process operation and control, and from the standpoint of process economics. In this program, an excess of about 5 mole % propene relative to the quantity of HBr fed was found highly effective, and thus a propene excess in the range of about 1 to about 2 mole % is deemed suitable for large scale operation.

At the conclusion of each run, the system was purged with helium to remove residual HBr and protect the HBr gas cylinder regulator, HBr flow controller, and other parts from corrosion.

In an extensive experimental program conducted using the laboratory-scale apparatus described above with reference to FIGS. 1 and 2, it was found that olefin ozonide catalysts made from $C_{10}$ or $C_{14}$ alpha-olefins when used at levels by weight of 7700 ppm ($C_{10}$–$C_{14}$ olefin ozonide/ propene fed) are capable of enabling propene hydrobromination products composed of 97% 1-bromopropane and 3% 2-bromopropane in 97% to 99% yield of these bromopropanes. Similar yields may be obtained with different catalyst concentrations and different operating conditions within the ranges reported herein. In contrast, use of benzoyl peroxide and tert-butyl perbenzoate were found to be substantially less effective as catalysts, requiring 4 wt % and 1.7 wt %, respectively to achieve comparable results. Moreover it was found that the process of this invention conducted on a continuous basis in the backflow reactor equipped with a packed absorption could be efficiently operated to 99 wt % HBr conversion, that excess propene gave process and economic advantages when using an excess as low as 3.8 to 5% of theoretical, that when using excess propene no evidence of propene dimerization or oligomerization was observed, that selectivity to 1-bromopropane remained constant at 97% throughout the range of 60° F. (ca. 16° C.) to 189° F. (ca. 88° C.), and that typical residence time to reach 99% HBr conversion was about 20 minutes, including the circulation time through the pump-around loop.

Figure 3:
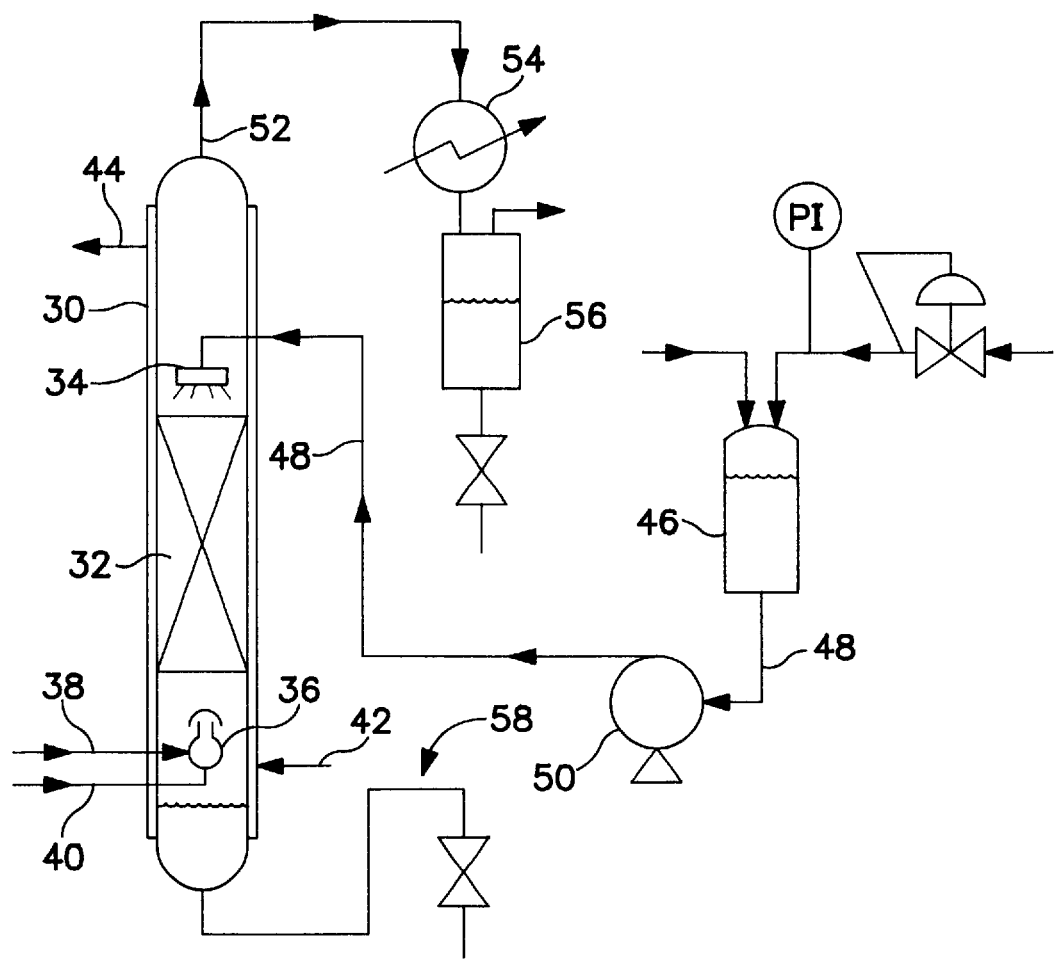
FIG. 3 is a schematic flow diagram of a process of this invention conducted in a reactive distillation column.

Turning now to the vapor phase system as depicted in FIG. 3, the hydrobromination reactor is composed of jacketed column 30 containing packed section 32, liquid distributor 34 disposed above section 32, and gas inlet venturi 36 disposed below section 32. Line 38 delivers gaseous hydrogen bromide to venturi 36. Gaseous propene is delivered to venturi 36 by line 40. Reaction temperature in column 30 is maintained by introduction of hot oil via line 42 at the lower region of the jacket of column 30 and withdrawal of the oil via line 44 at an upper region of the jacket. Ozonide catalyst dissolved in 1-bromopropane is delivered to distributor 34 from storage vessel 46 via line 48 and pump 50 thus establishing a countercurrent downward flow of catalyst and an upward flow of reactant vapors.

The hydrobromination product in the vapor state is taken by line 52 from the top of column 30 to condenser 54 and thence to product receiver tank 56. Condenser 54 is typically maintained at a temperature at or below about −30° C. (ca. −20° F.). Seal leg 58 is used to withdraw bottoms product from the sump of column 30. Preformed ozonide catalyst in storage vessel 46 is maintained under an anhydrous inert atmosphere such as dry nitrogen, argon, helium, or the like. Hydrobromination in a system such as this is most preferably performed at one or more temperatures in the range of about 165° F. (ca. 74° C.) to about 180° F. (ca. 83° C.) at about ambient atmospheric pressure.

Regardless of reactor type employed, the crude product contained some HBr, unreacted propene, propane, 2-bromopropane, 1-bromopropane, and by-products from the C14 ozonide. 1-Bromopropane of commercial purity was isolated.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. In short, the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process of producing 1-bromopropane which comprises forming a mixture from hydrogen bromide, propene and a catalytically effective amount of a preformed ozonide catalyst formed from one or more olefins that have at least 5 carbon atoms per molecule, and subjecting the mixture to or maintaining the mixture under reaction conditions effective to produce 1-bromopropane, such that 1-bromopropane is produced as at least the principal product of the reaction.

2. A process according to claim 1 wherein the hydrogen bromide and propene are proportioned such that there is a stoichiometric excess of propene relative to the hydrogen bromide.

3. A process according to claim 2 wherein the hydrogen bromide, propene and preformed ozonide catalyst are introduced into a liquid phase reaction mixture containing 1-bromopropane and optionally a small proportion of 2-bromopropane as well.

4. A process according to claim 2 wherein said preformed ozonide catalyst is introduced into a vapor phase mixture of hydrogen bromide and propene.

5. A process according to claim 4 wherein said preformed ozonide catalyst is introduced in the form of a spray or mist into a vapor phase mixture of hydrogen bromide and propene.

6. A process according to claim 5 wherein said preformed ozonide catalyst used in forming said spray or mist consists essentially of one or more olefin ozonides preformed from one or more olefins that have at least about 8 carbon atoms per molecule.

7. A process according to claim 5 wherein said preformed ozonide catalyst used in forming said spray or mist consists essentially of one or more olefin ozonides preformed from one or more $C_{14}$ olefins.

8. A process according to claim 4 wherein the vapor phase mixture of hydrogen bromide and propene is maintained at one or more temperatures in the range of about 10° C. to about 60° C. and at one or more pressures in the range of about 0 to about 60 psig effective to produce 1-bromopropane.

9. A process according to claim 8 wherein said one or more pressures are in the range of about 10 to about 30 psig.

10. A process which comprises reacting hydrogen bromide and propene in the presence of a preformed ozonide catalyst and/or one or more catalytic species or entities derived from the ozonide in, and as a consequence of, the conduct of the reaction, such that 1-bromopropane is produced, said preformed ozonide catalyst having been preformed from one or more olefins that have at least 5 carbon atoms per molecule.

11. A process according to claim 10 wherein the hydrogen bromide and propene are proportioned such that there is a stoichiometric excess of propene relative to the hydrogen bromide, and wherein the reaction is performed at least in part in the vapor phase, and wherein said preformed ozonide catalyst consists essentially of olefin ozonide preformed from one or more olefins that have at least about 8 carbon atoms per molecule.

12. A process according to claim 10 wherein the hydrogen bromide and propene are proportioned such that there is a stoichiometric excess of propene relative to the hydrogen bromide, and wherein the reaction is performed at least in part in the liquid phase, and wherein said preformed ozonide catalyst consists essentially of olefin ozonide preformed from one or more olefins that have at least about 8 carbon atoms per molecule.

13. A process which comprises subjecting a mixture formed from ingredients comprising 1-bromopropane, hydrogen bromide, propene and a catalytically effective amount of a preformed ozonide catalyst to reaction conditions effective to form 1-bromopropane, such that 1-bromopropane is formed, said hydrogen bromide and propene being proportioned such that there is a stoichiometric excess of propene relative to the hydrogen bromide, and said preformed ozonide catalyst having been preformed from one or more olefins that have at least about 5 carbon atoms per molecule.

14. A process according to claim 13 wherein said preformed ozonide catalyst as introduced into said mixture consists essentially of one or more olefin ozonides preformed from one or more olefins that have at least about 8 carbon atoms per molecule.

15. A process according to claim 13 wherein said mixture is subjected to one or more temperatures in the range of at least about 10° C. but below about 60° C. while at one or more pressures in the range of about 0 to about 60 psig.

16. A process according to claim 15 wherein said one or more pressures are in the range of about 10 to about 30 psig.

17. A process which comprises forming a liquid phase from ingredients consisting essentially of 1-bromopropane, hydrogen bromide, propene and a catalytically effective amount of a preformed ozonide catalyst, and subjecting the liquid phase to reaction conditions effective to form 1-bromopropane, such that additional 1-bromopropane is formed in said liquid phase, said preformed ozonide catalyst having been preformed from one or more olefins that have at least about 5 carbon atoms per molecule.

18. A process according to claim 17 wherein said preformed ozonide catalyst as introduced into said liquid phase consists essentially of one or more olefin ozonides formed from one or more olefins that have at least about 8 carbon atoms per molecule.

19. A process according to claim 17 wherein said liquid phase is subjected to one or more temperatures in the range of at least about 10° C. but below about 60° C., while at one or more pressures in the range of about 0 to about 60 psig.

20. A process according to claim 19 wherein said one or more pressures are in the range of about 10 to about 30 psig.

21. A process according to claim 17 wherein the process is conducted on a batch basis.

22. A process according to claim 17 wherein the process is conducted on a continuous basis.

23. A process according to claim 22 performed at a continuous conversion of propene to monobromopropane of at least 90%, with 1-bromopropane being at least 90% of the total monobromopropane produced.

24. A process according to claim 22 performed at a continuous conversion of propene to monobromopropane of at least 98%, with 1-bromopropane being at least 95% of the total monobromopropane produced.

* * * * *

UNITED STATES PATENT AND TRADEMARK OFFICE
CERTIFICATE OF CORRECTION

PATENT NO. : 5,773,672
DATED : Jun. 30, 1998
INVENTOR(S) : William B. Harrod, Alireza M. Dadgar, Phillip R. Beaver It is certified that error appears in the above-indentified patent and that said Letters Patent is hereby corrected as shown below:

Cover Sheet, Item [22] reads "Filed:   Jun. 20, 1997" and should read -- Filed:   Jun. 2, 1997 --.

Item [56]
Cover Sheet, Other Publications, title of first publication (Brouwer, et al.) reads "On the Addition of ... Bromide to Propane ... " and should read -- On the Addition of ... Bromide to Propene ... --.

Signed and Sealed this

Tenth Day of November 1998

Attest:

BRUCE LEHMAN

Attesting Officer

Commissioner of Patents and Trademarks